United States Patent
Jiang et al.

(10) Patent No.: US 11,649,511 B2
(45) Date of Patent: May 16, 2023

(54) MULTIPLEX PCR METHOD FOR THE DETECTION OF SARS-COV-2

(71) Applicant: DAAN Gene Co., Ltd., Guangdong (CN)

(72) Inventors: Xiwen Jiang, Guangdong (CN); Jian Fan, Guangdong (CN); Hailong Peng, Guangdong (CN); Rongyu Peng, Guangdong (CN)

(73) Assignee: DAAN GENE CO., LTD., Guangdong (CN)

( * ) Notice: Subject to any disclaimer, the term of this patent is extended or adjusted under 35 U.S.C. 154(b) by 282 days.

(21) Appl. No.: 16/760,945

(22) PCT Filed: Apr. 10, 2020

(86) PCT No.: PCT/CN2020/084231
§ 371 (c)(1),
(2) Date: May 1, 2020

(87) PCT Pub. No.: WO2021/155638
PCT Pub. Date: Aug. 12, 2021

(65) Prior Publication Data
US 2021/0404023 A1    Dec. 30, 2021

(30) Foreign Application Priority Data

Feb. 6, 2020    (CN) .......................... 202010078064.9

(51) Int. Cl.
*C12Q 1/70*    (2006.01)

(52) U.S. Cl.
CPC .... *C12Q 1/701* (2013.01); *C12N 2770/20011* (2013.01); *C12Q 2537/143* (2013.01); *C12Q 2600/16* (2013.01)

(58) Field of Classification Search
CPC .............. C12Q 1/701; C12Q 2537/143; C12Q 2600/16; C12N 2770/20011
See application file for complete search history.

(56) References Cited

U.S. PATENT DOCUMENTS

2005/0112558 A1    5/2005    Lo et al.

FOREIGN PATENT DOCUMENTS

| CN | 1450172 A | 10/2003 |
|---|---|---|
| CN | 103484565 A | 1/2014 |
| CN | 104846125 A | 8/2015 |
| CN | 107090519 A | 8/2017 |
| CN | 110273026 A | 9/2019 |
| WO | 2021152181 A | 8/2021 |

OTHER PUBLICATIONS

Lassauniere, R., et al., 2010, A novel multiplex real-time RT-PCR assay with FRET hybridization probes for the detection and quantitation of 13 respiratory viruses, J. Virol. Meth. 165:254-260.*
Huang et al.,"Clinical features of patients infected with 2019 novel coronavirus in Wuhan, China", www.thelancet.com, vol. 395, Issue 10223, p. 497-506, Feb. 15, 2020, cited in specification.
Lu et al., "Genomic characterisation and epidemiology of 2019 novel coronavirus: implications for virus origins and receptor binding", www.thelancet.com, vol. 395, Issue 10224, p. 565-574, Feb. 22, 2020, cited in specification.
International Search Report (with English translation) and Written Opinion issued in PCT/CN2020/084231, dated May 13, 2021, 14 pages provided.
The extended European search report issued in European Application No. 20786223.6, dated Dec. 6, 2021.
"Novel coronavirus nucleic acid determination primers and probe sequences" Institute for viral disease control and preventive, Chinese Center for Disease Control and Preven. Jan. 21, 2020, with English translation.
"Molecular assays to diagnose COVID-19: Summary table of available protocols", China CDC Primers and probes for detection 2019 nCoV, posted on Jan. 24, 2020, 80 pages.
Chu Daniel KW et al: "Molecular Diagnosis of a Novel Coronavirus (2019-nCoV) Causing an Outbreak of Pneumonia", Clinical Chemistry, vol. 66. No. 4. Jan. 31, 2020, pp. 549-555.

* cited by examiner

*Primary Examiner* — Jeffrey S Parkin
(74) *Attorney, Agent, or Firm* — Hamre, Schumann, Mueller & Larson, P.C.

(57) ABSTRACT

The present invention provides a novel coronavirus duplex detection kit. Specifically, the present invention discloses a kit and method for multiplex detection of novel coronavirus 2019-nCoV nucleic acid, which can simultaneously detect two nucleic acid targets of the novel coronavirus 2019-nCoV and possess extremely high sensitivity and specificity, and significantly improve the accuracy of virus identification.

13 Claims, 5 Drawing Sheets

Specification includes a Sequence Listing.

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial sequence
<220> FEATURE:
<223> OTHER INFORMATION: Primer

<400> SEQUENCE: 1
tcaaagtagc cactgtacag tc                                            22

<210> SEQ ID NO 2
<211> LENGTH: 19
<212> TYPE: DNA
<213> ORGANISM: Artificial sequence
<220> FEATURE:
<223> OTHER INFORMATION: Primer

<400> SEQUENCE: 2
ttagctaaga gaatgtcat                                                19

<210> SEQ ID NO 3
<211> LENGTH: 27
<212> TYPE: DNA
<213> ORGANISM: Artificial sequence
<220> FEATURE:
<223> OTHER INFORMATION: Probe

<400> SEQUENCE: 3
agtgcacatc agtagtctta ctctcag                                       27

<210> SEQ ID NO 4
<211> LENGTH: 18
<212> TYPE: DNA
<213> ORGANISM: Artificial sequence
```

```
<220> FEATURE:
<223> OTHER INFORMATION: Primer

<400> SEQUENCE: 4
tcttacaacc agaactca                                                    18

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
aggtaagaac aagtcctgag                                                  20

<210> SEQ ID NO 6
<211> LENGTH: 28
<212> TYPE: DNA
<213> ORGANISM: Artificial sequence
<220> FEATURE:
<223> OTHER INFORMATION: Probe

<400> SEQUENCE: 6
taattctttc acacgtggtg tttattac                                         28

<210> SEQ ID NO 7
<211> LENGTH: 19
<212> TYPE: DNA
<213> ORGANISM: Artificial sequence
<220> FEATURE:
<223> OTHER INFORMATION: Primer

<400> SEQUENCE: 7
agtattggag caccgtgcg                                                   19

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
gtggcggact cgccagttct                                                  20

<210> SEQ ID NO 9
<211> LENGTH: 23
<212> TYPE: DNA
<213> ORGANISM: Artificial sequence
<220> FEATURE:
<223> OTHER INFORMATION: Probe

<400> SEQUENCE: 9
atcgtaccta ggactctagc gcg                                              23

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
ctaaaatgtc agatgtaaag                                                  20
```

```
<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
tgtaactgga cacattgagc                                                     20

<210> SEQ ID NO 12
<211> LENGTH: 18
<212> TYPE: DNA
<213> ORGANISM: Artificial sequence
<220> FEATURE:
<223> OTHER INFORMATION: Primer

<400> SEQUENCE: 12
ttgtatcaaa gtagccac                                                       18

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
attgagccca caatttag                                                       18

<210> SEQ ID NO 14
<211> LENGTH: 117
<212> TYPE: DNA
<213> ORGANISM: Artificial sequence
<220> FEATURE:
<223> OTHER INFORMATION: Polyribonucleotide

<400> SEQUENCE: 14
agtattggag caccgtgcgg tcaacgtaag ggagcagagg cggcagtcaa ataacttcct         60
caaggaacaa cacgtaccta ggactctagc gcggactaga actggcgagt ccgccac          117

<210> SEQ ID NO 15
<211> LENGTH: 148
<212> TYPE: DNA
<213> ORGANISM: Artificial sequence
<220> FEATURE:
<223> OTHER INFORMATION: Polyribonucleotide

<400> SEQUENCE: 15
tcaaagtagc cactgtacag tctaaaatgt cagatgtaaa gtgcacatca gtagtcttac         60
tctcagtttt gcaacaactc agagtagaat catcatctaa attgtgggct caatgtgtcc       120
agttacacaa tgacattctc ttagctaa                                          148

<210> SEQ ID NO 16
<211> LENGTH: 144
<212> TYPE: DNA
<213> ORGANISM: Artificial sequence
<220> FEATURE:
<223> OTHER INFORMATION: Polyribonucleotide
```

-continued

```
<400> SEQUENCE: 16
tcttacaacc agaactcaat tacccggac tcgccagtct gcatacacta attctttcac      60
acgtggtgtt tattaccctg acaaagttct aggactctat tcagatcctc agttttacat    120
tcaactcagg acttgttctt acct                                            144
```

MULTIPLEX PCR METHOD FOR THE DETECTION OF SARS-COV-2

TECHNICAL FIELD

The present invention belongs to the field of biotechnology and molecular diagnosis. Specifically, the present invention relates to a primer and probe combination and a kit for detecting novel coronavirus 2019-nCoV.

BACKGROUND

Novel coronavirus (2019 novel corona virus, 2019-nCoV, SARS-CoV-2) belongs to the genus β-coronavirus, with an envelope, and the particles are round or elliptical, often polymorphic, with a diameter of 60~140 nm. S protein is one of the main proteins of the virus, and its coding gene is used for virus typing. Human respiratory epithelial cells were infected through the molecular mechanism of S-protein interacting with human ACE2. The common signs of people infected with the coronavirus are fever, cough, shortness of breath, difficulty breathing and the like. Severe infection can cause pneumonia, severe malformed respiratory syndrome, kidney failure, and even worse, it can lead to death. This novel coronavirus has a strong infectivity to humans, and the resulting lung infection is named as "Novel coronavirus pneumonia" (COVID-19).

At present, the main method of diagnosis of novel coronavirus infection is CT lung imaging. However, for the outbreak, it has the following defects:

1. CT is easy to cause cross-infection, unless a separate device that is completely enclosed is used, and disinfection is required at all times. For most epidemic areas, equipment and manpower cannot keep up with consumption;

2. There is also the possibility of misdiagnosis of CT positive. If it is a patient with ordinary flu, the CT image also has ground glass shadow;

3. CT instruments are expensive, and the remote and underdeveloped epidemic areas cannot be equipped with related instruments.

The fluorescence PCR method can make up for these deficiencies in detection. In Real-time fluorescence PCR technology, a pair of primers is added to a nucleic acid reaction tube and a specific fluorescent probe is added at the same time. The probe is an oligonucleotide, and a fluorescent reporter group and a fluorescent quenching group are labeled at both ends. When the probe is complete, the fluorescent signal emitted by the reporter group is absorbed by the quenching group. At the beginning, the probe is bound to any single strand of DNA and during PCR amplification, the 5'-3' exonuclease activity of the Taq enzyme degrade the probe by the digestion, so that the fluorescent reporter group and the fluorescent quenching group are separated. Then the fluorescence monitoring system can receive the fluorescent signal. That is, every time a DNA strand is amplified, a fluorescent molecule is formed. The accumulation of fluorescent signals and the formation of PCR products are completely synchronized. Fluorescence PCR technology is a nucleic acid detection technology with higher sensitivity, specificity and precision. The detection results are accurate, highly repeatable, and can reflect the changes of pathogens while avoiding the problem of post-processing required by traditional PCR reducing the possibility of contamination.

Based on this, it is very necessary to develop a set of products with high sensitivity, strong specificity and good repeatability for the detection of novel coronavirus nucleic acid.

SUMMARY OF THE INVENTION

The object of the present invention is to provide the novel coronavirus duplex detection kit, so that patients with novel coronavirus 2019-nCoV infection can be detected with high efficiency, high specificity and low cost.

In the first aspect of the present invention, it provides a primer pair set for detecting the novel coronavirus 2019-nCoV nucleic acid comprising:

a first primer pair group, wherein the first primer pair group comprises:

a forward primer as shown in SEQ ID NO. 1; and, a reverse primer as shown in SEQ ID NO. 2.

In another preferred embodiment, the primer pair set further includes:

a second primer pair group, wherein the second primer pair group comprises:

a forward primer as shown in SEQ ID NO. 4; and, a reverse primer as shown in SEQ ID NO. 5.

In another preferred embodiment, the primer pair set further comprises:

an internal standard primer pair group, wherein the internal standard primer pair group comprises:

a forward primer as shown in SEQ ID NO. 7; and, a reverse primer as shown in SEQ ID NO. 8.

In the second aspect of the present invention, it provides a probe set for multiple detection of the novel coronavirus 2019-nCoV nucleic acid, which includes a first probe whose nucleotide sequence is shown in SEQ ID NO. 3.

In another preferred embodiment, the probe set further includes a second probe whose nucleotide sequence is shown in SEQ ID NO. 6.

In another preferred embodiment, the probe set further includes an internal control probe whose nucleotide sequence is shown in SEQ ID NO. 9.

In another preferred embodiment, the 5' end of each probe contains a fluorescent reporter group; and/or, the 3' end of each probe contains a fluorescence quenching group.

In another preferred embodiment, the fluorescent reporter groups labeled on the probes are different from each other.

In the third aspect of the present invention, it provides a kit for multiple detection of the novel coronavirus 2019-nCoV nucleic acid, which comprises the primer pair set according to the first aspect of the present invention.

In another preferred embodiment, the kit further includes the probe set according to the second aspect of the present invention.

In another preferred embodiment, the kit includes a first container, and the first container contains a primer and probe mix (primer-probe mixture), and the primer and probe mix contains polynucleotide sequences as shown in SEQ ID NO. 1-6.

In another preferred embodiment, the kit includes a first container, and the first container contains a primer and probe mix, and the primer and probe mix further contains polynucleotide sequences as shown in SEQ ID NO. 7-9.

In another preferred embodiment, the primer and probe mix is prepared using a buffer for PCR (Buffer).

In another preferred embodiment, the kit further includes a second container, and the second container contains a PCR enzyme system including a hot-start enzyme and a reverse transcriptase C-MMLV; preferably further includes RNase inhibitor.

In another preferred embodiment, the kit further includes a third container, and the third container contains a positive quality control product.

In another preferred embodiment, the kit further includes a fourth container, and the fourth container contains a negative control product.

In the fourth aspect of the present invention, it provides a method for multiple detection of the novel coronavirus 2019-nCoV nucleic acid, which includes the steps of:

(1) providing a nucleic acid sample of a subject to be tested;

(2) preparing a PCR reaction system for the PCR detection, wherein the PCR reaction system includes: the nucleic acid sample provided in step (1), the primer pair set according to the first aspect of the present invention, and the probe set according to the second aspect of the present invention.

In another preferred embodiment, the nucleic acid sample may be from a pharyngeal swab sample, alveolar lavage fluid sample, blood sample, sputum sample, or environmental sample.

In another preferred embodiment, the method is a detection method for non-diagnostic purposes.

In another preferred embodiment, the PCR reaction system further includes a positive quality control product, and/or a negative quality control product.

In another preferred embodiment, the PCR reaction system further includes a PCR enzyme system.

In a fifth aspect of the present invention, it provides a use of the primer pair set according to the first aspect of the present invention, and/or the probe set according to the second aspect of the present invention for preparing a PCR detection kit, the PCR detection kit is used to detect the novel coronavirus 2019-nCoV nucleic acid.

It should be understood that, within the scope of the present invention, the technical features specifically described above and below (such as the Examples) can be combined with each other, thereby constituting a new or preferred technical solution which needs not be described one by one.

DETAILED DESCRIPTION OF INVENTION

Figure 1:
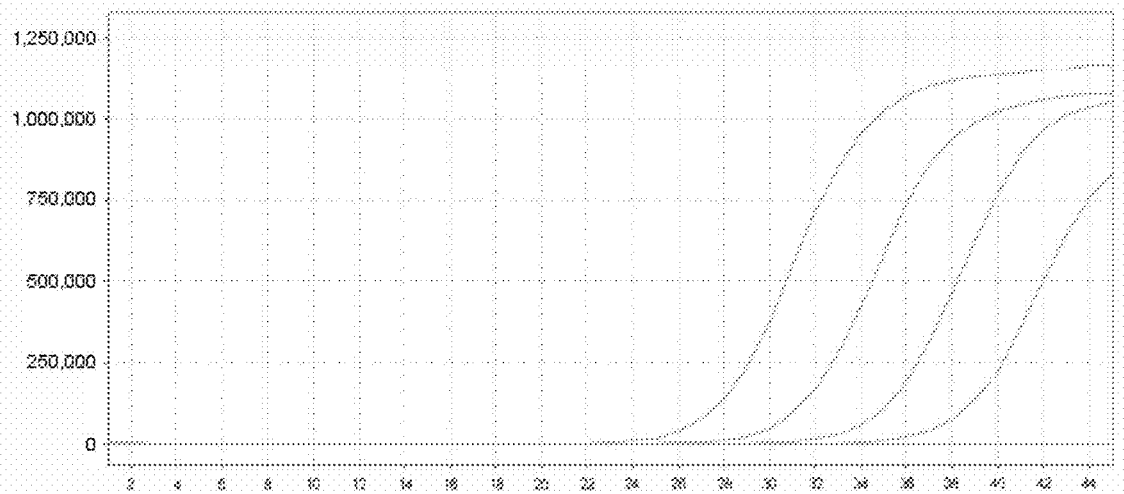
FIG. 1: Detection limit for ORF1ab gene.

Through extensive and intensive research, the present inventor has obtained a kit and method for multiple detection of the novel coronavirus 2019-nCoV nucleic acid, which can simultaneously detect the two nucleic acid targets of the novel coronavirus 2019-nCoV and mutual verification between different targets can be used to prevent false positives and to confirm missed detections that may be caused by mutations, which significantly improves the accuracy of virus identification.

Before describing the present invention, it should be understood that the present invention is not limited to the specific methods and experimental conditions as described, due to such methods and conditions may vary. It should also be understood that the terminology used herein is for the purpose of describing specific embodiments only and is not intended to be limiting, and the scope of the present invention will be limited only by the appended claims.

Unless otherwise defined, all technical and scientific terms used herein have the same meaning as commonly understood by those of ordinary skill in the art to which this invention belongs. As used herein, when used in reference to specifically recited values, the term "about" means that the value may vary from the recited value by no more than 1%. For example, as used herein, the expression "about 100" includes all values between 99 and 101 and (e.g., 99.1, 99.2, 99.3, 99.4, etc.).

Although any methods and materials similar or equivalent to those described in the present invention can be used in the practice or testing of the present invention, the preferred methods and materials are exemplified herein.

Multiplex PCR

Multiplex PCR, also known as multiple primers PCR or complex PCR, is a PCR reaction in which two or more pairs of primers are added to the same PCR reaction system to simultaneously amplify multiple nucleic acid fragments. The reaction principle, reaction reagents and operation process are the same as general PCR.

There are many factors that affect multiplex PCR reactions, such as:

(1) The imbalance of the reaction system. The imbalance of the reaction system leads to the rapid amplification of certain dominant primers and their templates in the previous rounds of reactions, and a large number of amplification products are obtained, and these amplification products are also good inhibitors of DNA polymerase. Therefore, as a large number of amplification products appear, the polymerization ability of the polymerase is more and more strongly inhibited. Therefore, the primers and their templates that are at a disadvantage in the early stage are more difficult to react, resulting in a very small amount of amplification product that cannot be detected.

(2) Primer specificity. If the primer has stronger binding ability with other non-target gene fragments in the system, the ability of the target gene to bind to the primer will be contested, resulting in a decrease in amplification efficiency.

(3) The optimal annealing temperature is inconsistent. Multiple pairs of primers are put into a system for amplification. Since the annealing temperature for PCR reaction is the same, the optimal annealing temperature of each pair of primers is required to be close.

(4) Primer dimers, including the dimers between primers and the hairpin structure formed by the primers themselves, and there is also a third-party DNA-mediated polymer. Like non-specific primers, these dimers will interfere with the competition between the primer and the target binding site, affecting the amplification efficiency.

Although several factors affecting the efficiency of amplification are mentioned as above, more factors are unclear. So far, there is no effective method that can clearly predict the amplification efficiency.

According to the diagnosis and treatment guidelines for novel coronavirus, nucleic acid detection of novel coronavirus is the gold standard for diagnosis. The present invention develops a detection kit for simultaneously detecting the ORF1ab gene and N gene of the novel coronavirus. The kit also includes an endogenous internal standard detection system, which is used to monitor specimen collection, nucleic acid extraction process and PCR amplification process, to reduce the occurrence of false negative results. The kit is a dual fluorescence detection kit, which has the characteristics of high sensitivity, strong specificity and good repeatability.

The present invention provides a primer/probe combination for specifically detecting the ORF1ab gene and N gene in a sample and a kit containing the primer combination, wherein the primer sequences for detecting the ORF1ab gene are:

```
SEQ ID NO. 1:
TCAAAGTAGCCACTGTACAGTC
and

SEQ ID NO. 2:
TTAGCTAAGAGAATGTCAT,
```

The corresponding detection probe sequence is SEQ ID NO. 3: AGTGCACATCAGTAGTCTTACTCTCAG;

The primer sequences used to detect the N gene are:

```
SEQ ID NO. 4:
TCTTACAACCAGAACTCA
and

SEQ ID NO. 5:
AGGTAAGAACAAGTCCTGAG,
```

The corresponding detection probe sequence is: SEQ ID NO. 6 TAATTCTTTCACACGTGGTGTTTATTAC.

The probe labels of the pathogens of the present invention are not limited to the single labels listed at the same wavelength, and include multiple detection reagents in different combinations of different labels.

In one embodiment, the kit further includes internal standard quality control and amplification primers and detection probes; the internal standard quality control amplification primer sequences are:

```
SEQ ID NO. 7:
AGTATTGGAGCACCGTGCG
and

SEQ ID NO. 8:
GTGGCGGACTCGCCAGTTCT,
```

The corresponding detection probe sequence is SEQ ID NO. 9: ATCGTACCTAGGACTCTAGCGCG.

The internal standard can monitor the sample collection and the sample extraction process to prevent false negatives due to the failure of sample nucleic acid extraction.

In a preferred embodiment of the present invention, the nucleic acid sequence of the internal standard fragment is as follows:

```
                                       (SEQ ID NO: 14)
AGTATTGGAGCACCGTGCGGTCAACGTAAGGGAGCAGAGGCGGCAG

TCAAATAACTTCCTCAAGGAACAACACGTACCTAGGACTCTAGCGCGGA

CTAGAACTGGCGAGTCCGCCAC.
```

In one embodiment, the kit includes a positive control containing the ORF1ab gene fragment and/or N gene fragment, and a negative control (sterilized physiological saline).

In a preferred embodiment of the present invention, the nucleic acid sequence of the ORF1ab gene fragment in the positive control is as follows:

```
                                      (SEQ ID NO.: 15)
TCAAAGTAGCCACTGTACAGTCTAAAATGTCAGATGTAAAGTGCACA

TCAGTAGTCTTACTCTCAGTTTTGCAACAACTCAGAGTAGAATCATCAT

CTAAATTGTGGGCTCAATGTGTCCAGTTACACAATGACATTCTCTTAGC

TAA.
```

In a preferred embodiment of the present invention, the nucleic acid sequence of the N gene fragment in the positive control is as follows:

```
                                      (SEQ ID NO.: 16)
TCTTACAACCAGAACTCAATTACCCCGGACTCGCCAGTCTGCATACA

CTAATTCTTTCACACGTGGTGTTTATTACCCTGACAAAGTTCTAGGAC

TCTATTCAGATCCTCAGTTTTACATTCAACTCAGGACTTGTTCTTACC

T.
```

In one embodiment, the kit includes PCR reaction solution containing primers and probes targeting ORF1ab gene and N gene and internal standard gene, dNTPs (dATP:dCTP:dGTP:dTTP=1:1:1:1) and PCR buffer, and PCR enzyme system containing hot start Hot.Taq enzyme and C-MMLV enzyme, in which the concentration of primers and probes is 0.1-1 μM, the concentration of dNTPs is 0.2-0.4 mM, the concentration of $MgCl_2$ is 2-5 mM, C-MMLV enzyme is 1-3U and the hot start Hot.taq is 2.5-10U.

The invention also provides a method for using the ORF1ab gene and N gene double detection kit, which includes the following steps: extracting a sample to be tested (extraction reagent adopts nucleic acid extraction or purification reagent produced by Daan Gene Co., Ltd. of Sun Yat-sen University (Yuehuixiebei No. 20170583) to obtain nucleic acid samples (positive quality control and negative control participate in the extraction at the same time); taking 5 μL into the above PCR reaction solution (17 μL) and enzyme (3 μL) mixture, and the amplification reaction in a real-time fluorescent PCR instrument is performed, selecting the fluorescence channel in order of VIC, FAM, and Cy5. The PCR amplification procedure is as follows;
50° C., 15 min, 95° C., 15 min; 1 cycle
94° C., 15 sec, 55° C., 45 sec (collecting fluorescence); 45 cycles.

After PCR is completed, different fluorescent channel curves and Ct values are used to determine the negative or positive of the corresponding pathogen DNA. The test results can be used for the auxiliary diagnosis of novel coronavirus infection and the observation of drug efficacy, providing a reliable basis for the research.

For the gene sequence of the novel coronavirus 2019-nCoV in the present invention, please refer to GISAID: BetaCov/Wuhan/WH01/2019|EPI_ISL_406798; for the oligonucleotide sequence information of its N, ORF1ab and E genes, please refer to the literature (Roujian Lu, Xiang Zhao, Juan Li, et. al, Genomic characterisation and epidemiology of 2019 novel coronavirus: implications for virus origins and receptor binding. Lancet. 2020 Jan. 30).

The composition of this kit is detailed in Table 1 and Table 2. It can detect two target genes of the novel coronavirus 2019-nCoV at the same time, and can verify each other through different targets to prevent false positives and to confirm the missed detection that may be caused by mutation, which can significantly improve the accuracy of virus identification

TABLE 1

Kit composition

| Composition | Main component |
|---|---|
| PCR reaction solution | Specific primers and fluorescent probes (SEQ ID NO.: 1-9), dNTPs, PCR buffer |
| PCR enzyme system | Hot start Hot.Taq enzyme, reverse transcriptase C-MMLV |
| Positive quality control | Pseudovirus containing ORF1ab gene fragment, Pseudovirus containing N gene fragment, Pseudovirus containing internal standard fragment |
| Negative quality control | Pseudovirus containing internal standard fragments |

The primer and probe sequences required by the kit are shown in Table 2:

TABLE 2

Primers, probes and serial numbers

| Primer/probe name | Primer/probe sequence | SEQ ID NO. |
|---|---|---|
| ORF1ab-F1 | TCAAAGTAGCCACTGTACAGTC | 1 |
| ORF1ab-R1 | TTAGCTAAGAGAATGTCAT | 2 |
| ORF1ab-P | 5'VIC-AGTGCACATCAGTAGTCTTACTCTCAG BHQ1-3' | 3 |
| N-F1 | TCTTACAACCAGAACTCA | 4 |
| N-R1 | AGGTAAGAACAAGTCCTGAG | 5 |
| N-P | 5'FAM-TAATTCTTTCACACGTGGTGTTTATTAC BHQ1-3' | 6 |
| Internal standard-F1 | AGTATTGGAGCACCGTGCG | 7 |
| Internal standard-R1 | GTGGCGGACTCGCCAGTTCT | 8 |
| Internal standard-P | 5'Cy5-ATCGTACCTAGGACTCTAGCGCG-BHQ2-3' | 9 |

Preferably, the fluorescent group is selected from the group consisting of FAM, VIC, HEX, NED, ROX, TET, JOE, TAMRA, CY3, CY5.

Preferably, the quenching group is selected from the group consisting of MGB, BHQ-1, BHQ-2, BHQ-3.

In the primer design of the present invention, specific primers and probes are screened through a large number of tests, and combined, optimized, and verified. The optimal combination of primers and probes for multiple detection that does not interfere with each other, has high amplification efficiency and good specificity is finally selected.

The criteria used by the kit of the present invention to determine the effectiveness of the detection are:

Negative quality control and positive quality control are simultaneously detected in each test. When the test result of the positive quality controls positive and the test result of the negative quality control is negative, the test result is valid.

The method for using the kit of the present invention includes the following steps:

(1) Extracting the total nucleic acid in the test sample to obtain a nucleic acid sample.

(2) Mixing the nucleic acid sample with the PCR reaction solution and PCR enzyme system to prepare a PCR reaction system.

(3) Performing Real-time fluorescence PCR reaction, and the procedure is as follows:

the first stage: 50° C. 2-15 min, 95° C. 10-15 min, 1 cycle;

the second stage: 94° C. 10-15 s, 55-60° C. 45 s, 45 cycles.

After the PCR is completed, the negative and positive of the corresponding pathogen nucleic acid are judged by different fluorescence channel curves and Ct values, to obtain the test result.

The Beneficial Effects of the Present Invention Include:

Most of the current detection reagents are single-target detection reagents. The two targets of the novel coronavirus 2019-nCoV are tested at the same time, so they can be mutually verified between different targets to prevent false positives and significantly improve the accuracy and specificity of virus identification. At the same time, the system contains an endogenous internal standard quality control system, which can monitor the entire process of sampling, sample storage, nucleic acid extraction and PCR amplification to prevent the occurrence of false negatives.

The present invention is suitable for the detection of the novel coronavirus 2019-nCoV nucleic acid, and can provide a reliable basis for virus identification and prevention and control, and is worthy of popularization and application. In addition, the method of the present invention is also suitable for non-diagnostic purposes. For example, in the epidemic prevention and control process, the detection method of the present invention can be used to detect viral nucleic acids in the environment, and these viral nucleic acid information can be used for public health management.

The present invention will be further described in detail below in conjunction with specific embodiments. It should be understood that these examples are only used to illustrate the present invention and not to limit the scope of the present invention. The experimental methods without detailed conditions in the following examples are generally in accordance with the conditions described in the conventional conditions such as Sambrook. J et al. "Guide to Molecular Cloning Laboratory" (translation by Huang Peitang et al., Beijing: Science Press, 2002), Or as recommended by the manufacturer. Unless otherwise stated, percentages and parts are calculated by weight. Unless otherwise specified, the experimental materials and reagents used in the following examples can be obtained from commercially available channels.

Example 1. Detection Limit Test of ORF1ab Gene and N Gene Duplex Detection Kit

Figure 2:
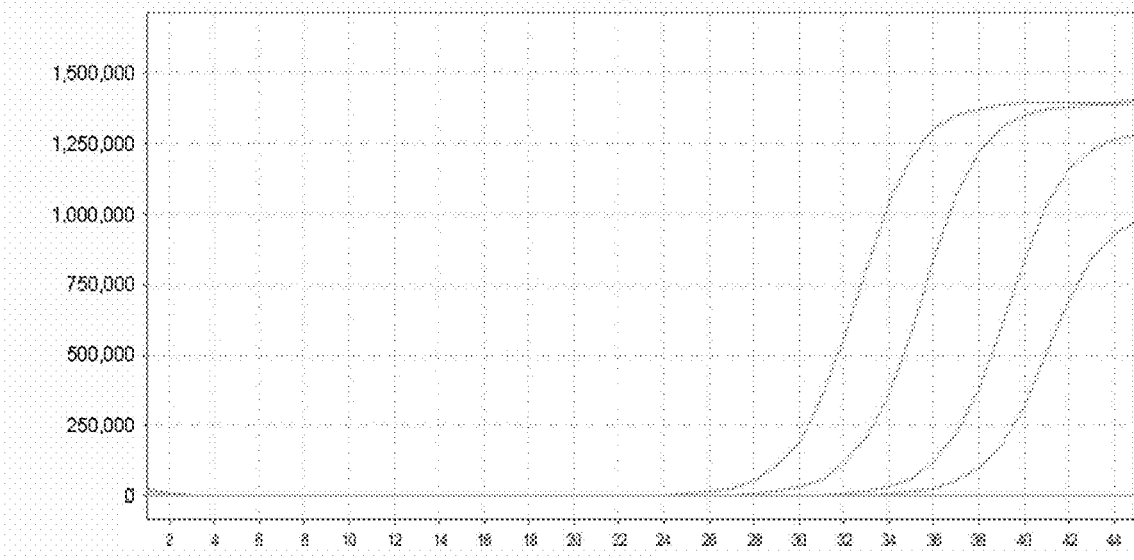
FIG. 2: Detection limit for N gene.
Figure 3:
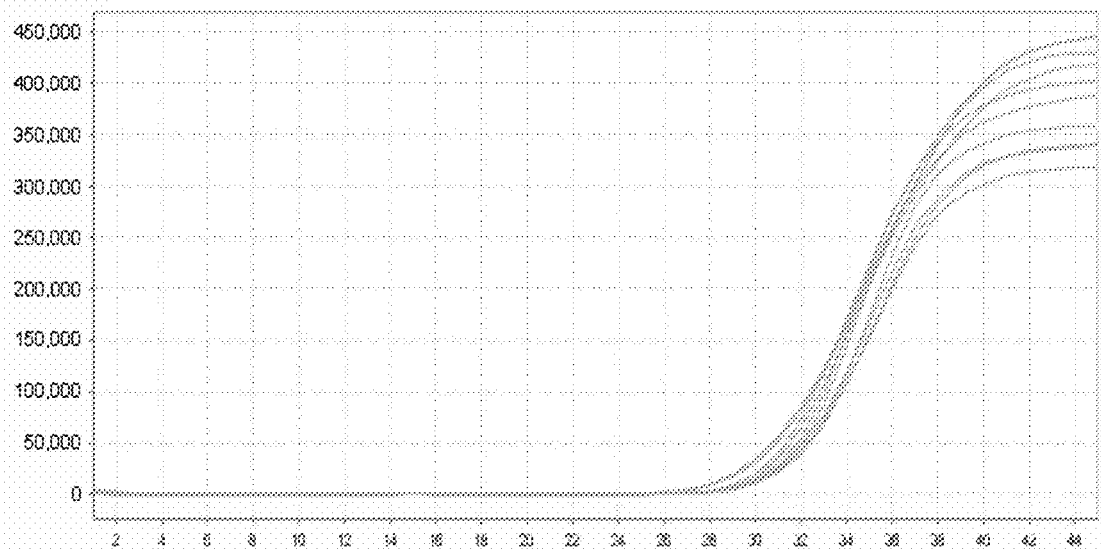
FIG. 3: Internal standard test results.

The quantified pseudovirus containing ORF1ab gene and N gene were used as the initial samples and were diluted to a concentration of $10^5$ copies/ml, and then sequentially diluted to $10^4$, $10^3$, 500, 250, 100 copies/ml, and the plasmid bacteria containing the internal standard amplified fragments were added into each samples to a final concentration of $10^4$ copies/ml as the samples to be tested to test the sensitivity of the dual detection reagent.
Refer to FIGS. 1-3 for test results:
FIG. 1: detection limit for ORF1ab gene;
FIG. 2: detection limit for N gene;
FIG. 3: internal standard test results.
The test results showed that the lowest concentration that can be detected for the positive control of ORF1ab gene and N gene at different concentrations was 250 copies/ml.

Example 2. Specificity Test of ORF1ab Gene and N Gene Duplex Detection Kit

Figure 4:
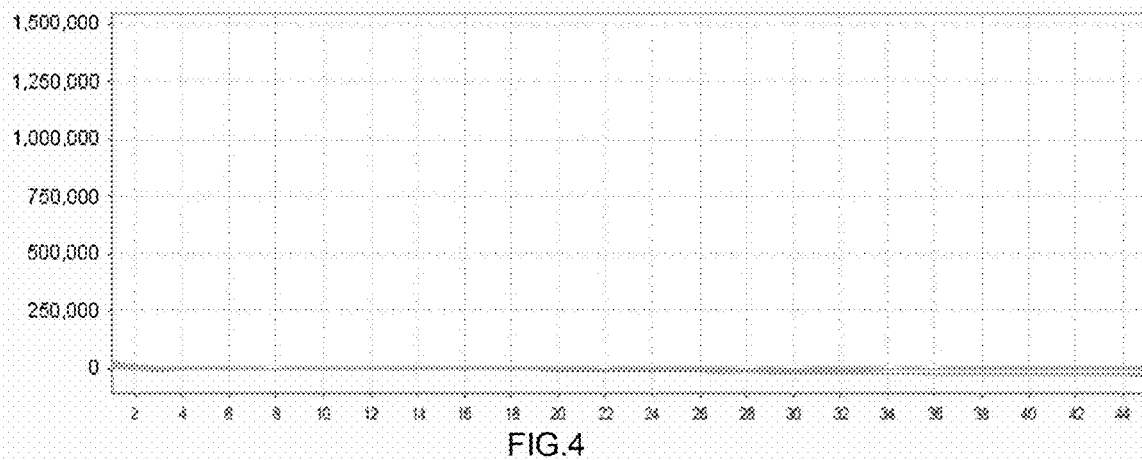
FIG. 4: Specific test results for ORF1ab gene and N gene.
Figure 5:
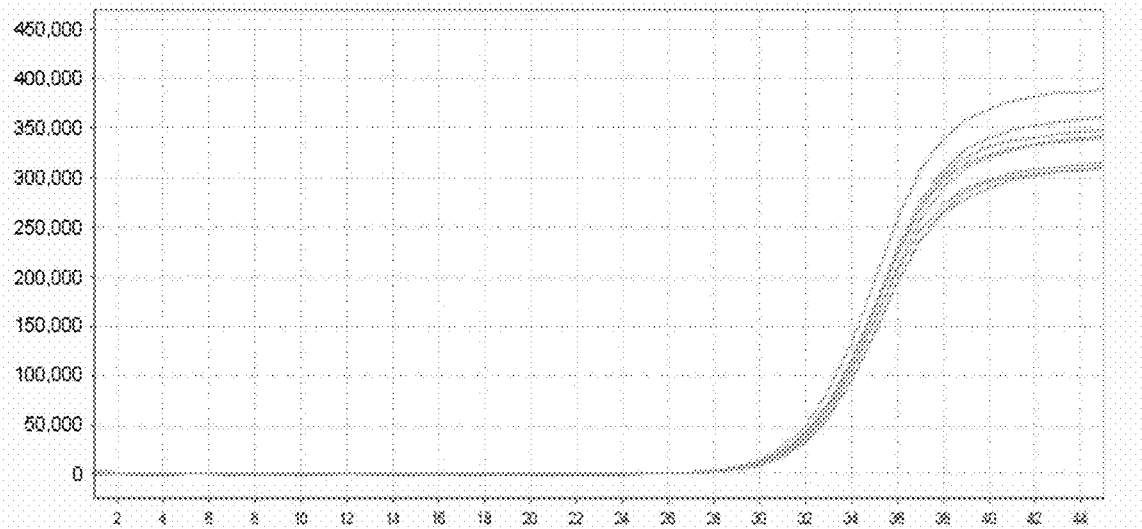
FIG. 5: Internal standard test results in ORF1ab gene and N gene specific detection.

Using saline, SARS virus, rhinovirus, adenovirus, influenza A virus, influenza B virus, parainfluenza virus, coronavirus OC43, respiratory syncytial virus, human coronavirus NL63, human coronavirus HKU1 as specificity references, the specificity of the ORF1ab gene and N gene duplex detection kits was tested.
Refer to FIGS. 4-5 for test results:
FIG. 4: ORF1ab gene and N gene specificity test results;
FIG. 5: Internal standard test results in ORF1ab gene and N gene specificity test.
The test results showed that the test results of specificity references (physiological saline, SARS virus, rhinovirus, adenovirus, influenza A virus, influenza B virus, parainfluenza virus, coronavirus OC43, respiratory syncytial virus, human coronavirus NL63, Human coronavirus HKU1) are all negative, and the test results of internal standard quality control are all positive.

Example 3. Precision Test of ORF1ab Gene and N Gene Duplex Detection Kit

Figure 6:
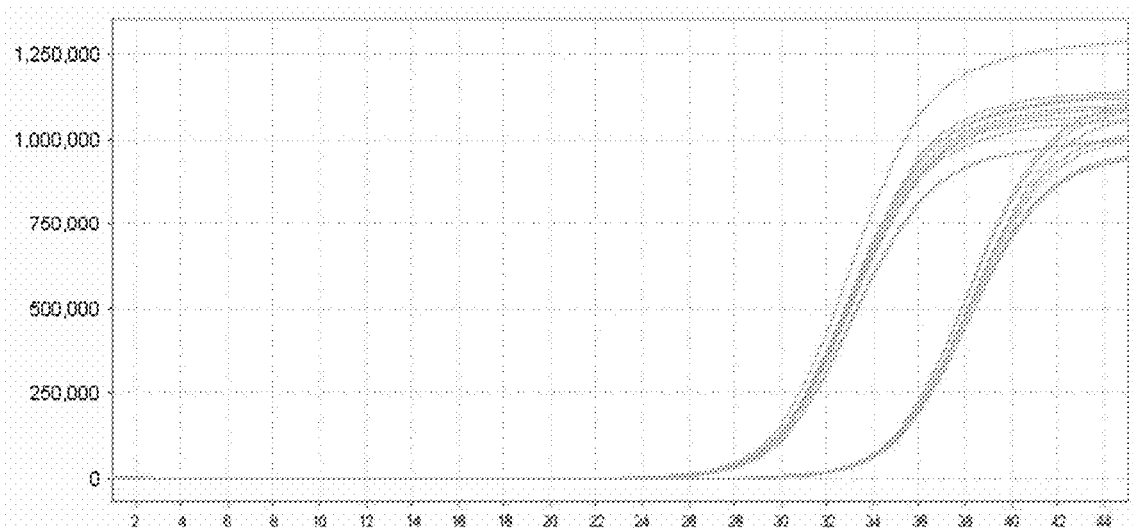
FIG. 6: Precision detection results for ORF1ab gene.
Figure 7:
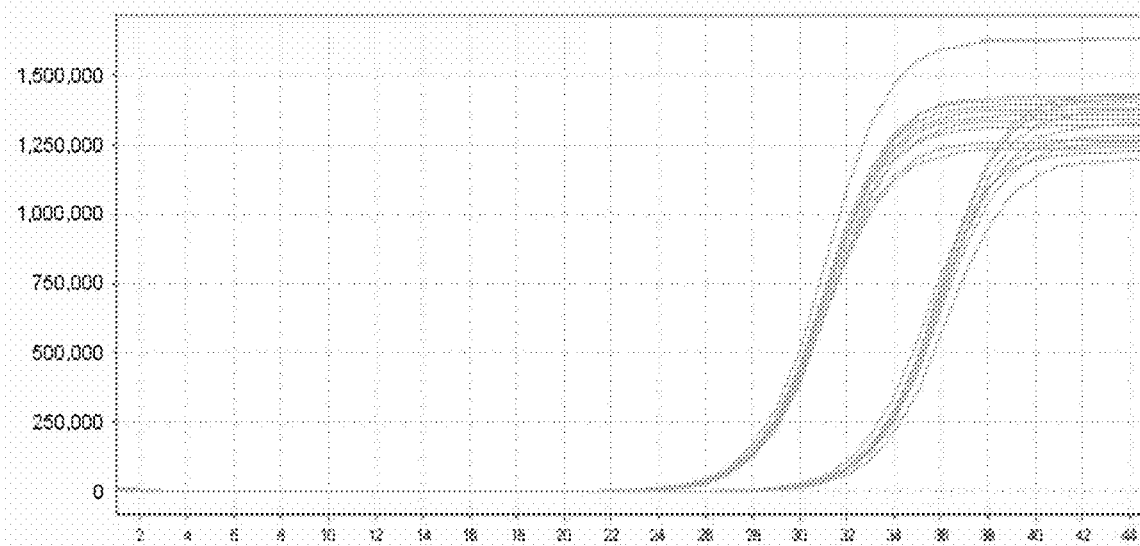
FIG. 7: Precision detection results for N gene.

Pseudovirus containing ORF1ab gene and N gene was diluted into $10^5$ and $10^3$ copies/ml as precision references. Test was repeated 10 times to calculate the variable coefficient of each concentration of precision reference.
Refer to FIG. 6-7 for test results:
FIG. 6: ORF1ab gene precision test results
FIG. 7: N gene precision test results
After testing, the variable coefficient of the precision reference with high concentration and low concentration of ORF1ab gene pseudovirus were 0.55% and 0.65%, respectively. the variable coefficient of the precision reference with high concentration and low concentration of N gene were 0.44% and 0.96%, respectively. The variable coefficients of the precision reference with different concentrations of the two gene were less than 5%.

Example 4. Accuracy Test of ORF1ab Gene and N Gene Duplex Detection Kit

Figure 8:
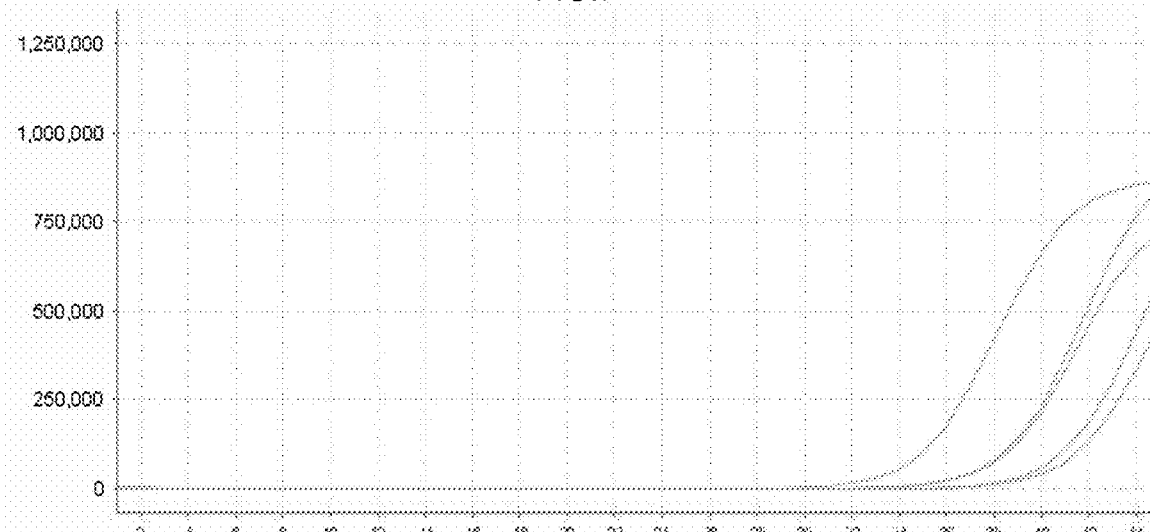
FIG. 8: Accuracy detection results for ORF1ab gene.
Figure 9:
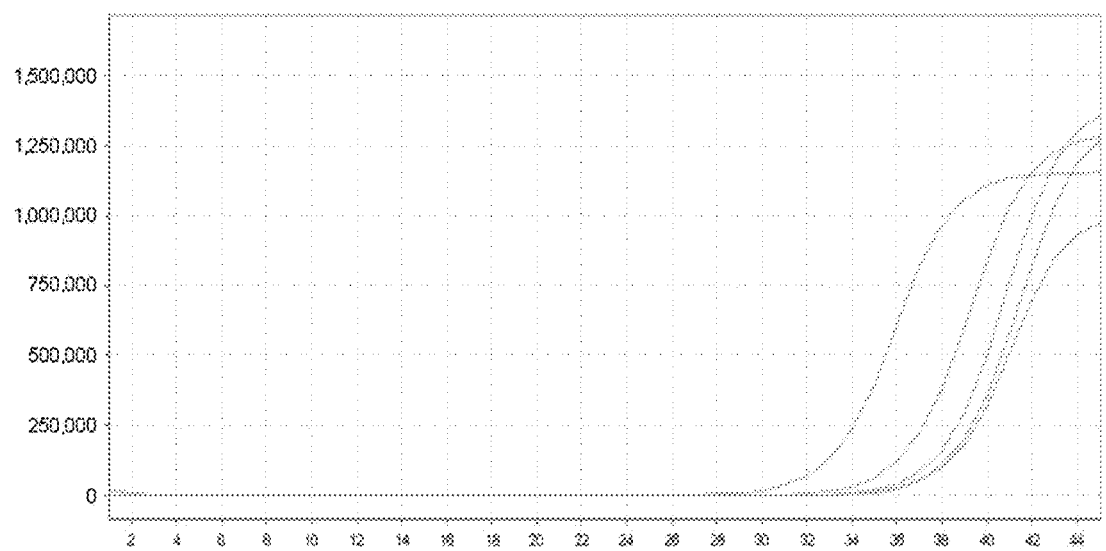
FIG. 9: Accuracy detection results for N gene.

Five different concentrations of ORF1ab gene and N gene pseudovirus were respectively prepared as positive references. After extraction, the ORF1ab gene and N gene duplex detection kits were used to test and verify the accuracy of the kits.
Refer to FIGS. 8-9 for test results:
FIG. 8: ORF1ab gene accuracy test results;
FIG. 9: N gene accuracy test results.
The results showed that the positive references of each pathogen were positive and did not cross-react with other pathogens.

Figure 10:
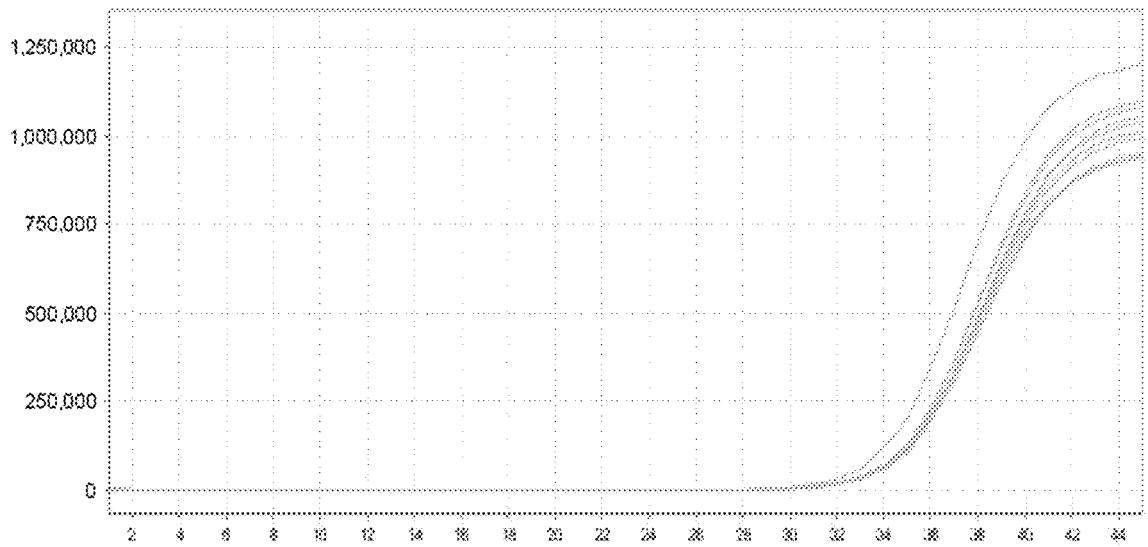
FIG. 10: Interference detection results for ORF1ab gene.
Figure 11:
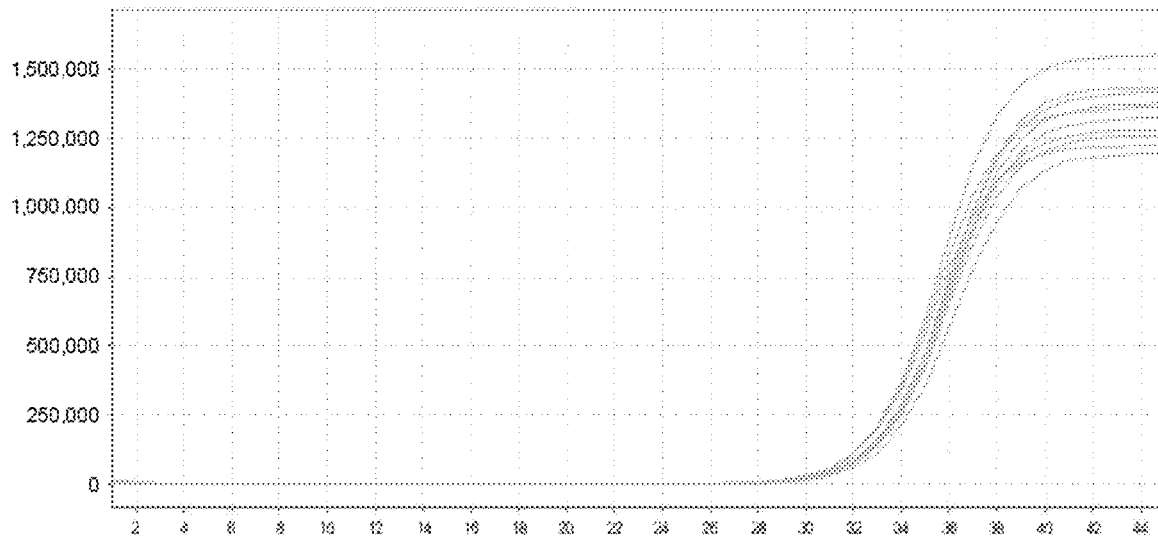
FIG. 11: Interference detection results for N gene.

Example 5. Interfering Substance Test of ORF1ab Gene and N Gene Duplex Detection Kit Whole blood (5%), mucus (5%), spectinomycin (100 mg/L), penicillin (0.5 mg/ml), tetracycline (5 mg/L), ofloxacin (3.06 mg/L), and azithromycin (0.45 mg/L) were separately added into $10^3$ copies/ml of ORF1ab gene and N gene pseudovirus as interfering substance in the test, and samples without interfering substances were used as controls to test the effect of interfering substances on the amplification of primer and probes.
Refer to FIGS. 10-11 for test results:
FIG. 10: ORF1ab gene interference detection results
FIG. 11: N gene interference detection results
Whole blood (5%), mucus (5%), spectinomycin (100 mg/L), penicillin (0.5 mg/ml), tetracycline (5 mg/L), ofloxacin (3.06 mg/L), azithromycin (0.45 mg/L) were added to the sample to be tested. The results showed that there were no obvious interference to the test results, and the interpretation of the results were not affected.

Example 6. Clinical Sample Testing

Figure 12:
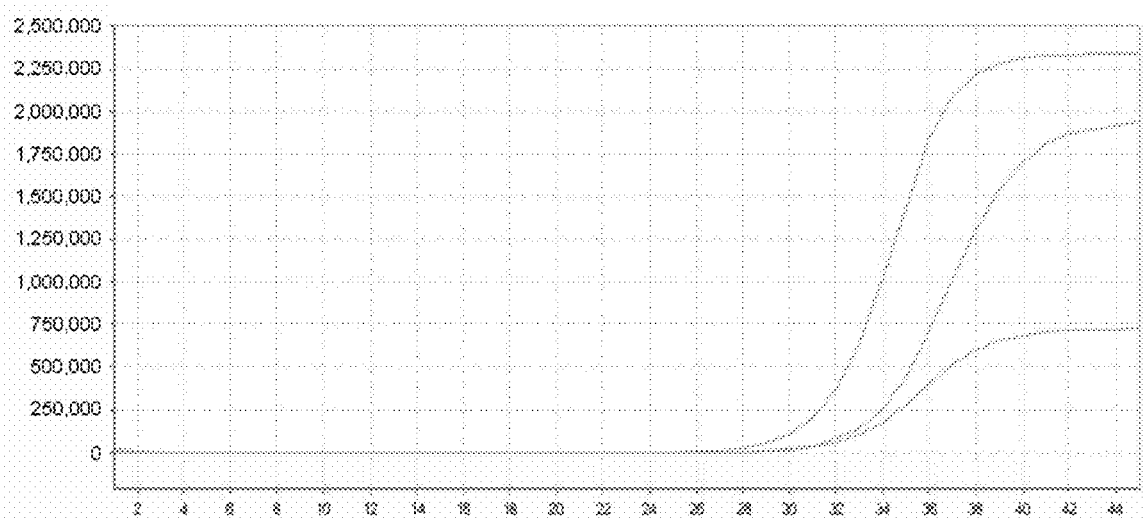
FIG. 12: Detection results of clinical samples.

Extraction of Test Sample Nucleic Acids:
(1) Extraction of Nucleic Acid Template of Clinical Samples
22 clinical samples of suspected pharyngeal swabs were collected, and the samples to be tested were extracted (the extraction reagent adopts the nucleic acid extraction or purification reagent produced by Daan Gene Co., Ltd. of Sun Yat-sen University (Yuehuixiebei No. 20170583) to obtain nucleic acid samples (the positive quality control and the negative control were involved in the extraction simultaneously). 5 µL of nucleic acid samples was added to the above PCR reaction solution (17 µL) and the enzyme (3 µL) mixture, and the amplification reaction was performed in the real-time fluorescent PCR instrument, and the fluorescent channels were selected in order of VIC, FAM, and Cy5. The PCR amplification procedure was as follows:
50° C., 15 min, 95° C., 15 min; 1 cycle
94° C., 15 sec, 55° C., 45 sec (collection of fluorescence); 45 cycles.
After the PCR was completed, the negative and positive of the corresponding pathogen DNA were determined by different fluorescence channel curves and Ct values.
In the tested 22 suspected clinical samples, a total of 17 novel coronavirus 2019-nCoV nucleic acid positive clinical samples were detected. Typical test results were shown in FIG. 12.

Sequencing verification results showed that the detection accuracy of the detection system of the present invention reached 100%, which further proved the accuracy of clinical detection of the system of the present invention.

Comparative Example 1

In the research process, the present inventor screened dozens of PCR primers and probes for the novel coronavirus 2019-nCoV target nucleic acid sequence. After extensive testing, a combination of primers and probes with sensitivity and specificity that can meet the needs of clinical testing and can perform multiple tests were finally obtained.

For the detection target of the N, ORF1ab gene of the novel coronavirus 2019-nCoV, the present inventor had undergone a lot of screening and combination. For example, for the ORF1ab gene, some typical primer sequences designed were as follows:

```
ORF1ab gene control upstream primer ORF1ab-F2:
                                    (SEQ ID NO. 10)
CTAAAATGTCAGATGTAAAG ORF1ab gene control downstream primer ORF1ab-R2:
                                    (SEQ ID NO. 11)
TGTAACTGGACACATTGAGC ORF1ab gene control upstream primer ORF1ab-F3:
                                    (SEQ ID NO. 12)
TTGTATCAAAGTAGCCAC ORF1ab gene control downstream primer ORF1ab-R3:
                                    (SEQ ID NO. 13)
ATTGAGCCCACAATTTAG
```

The specific detection steps, detection conditions, and probe sequences were same as the above embodiments, and PCR detection tests are performed.

Figure 13:
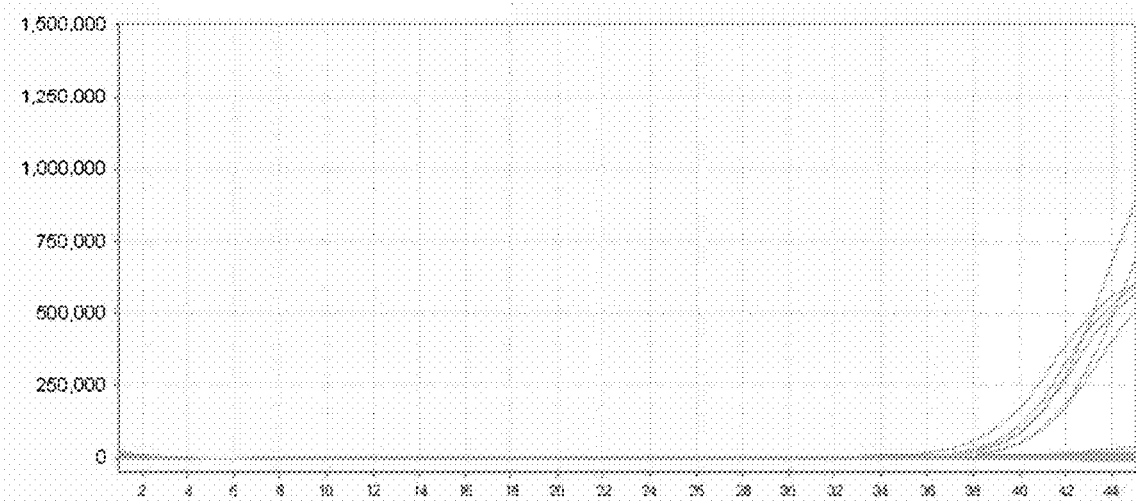
FIG. 13: Detection results for ORF1ab gene using control primer pair.
Figure 14:
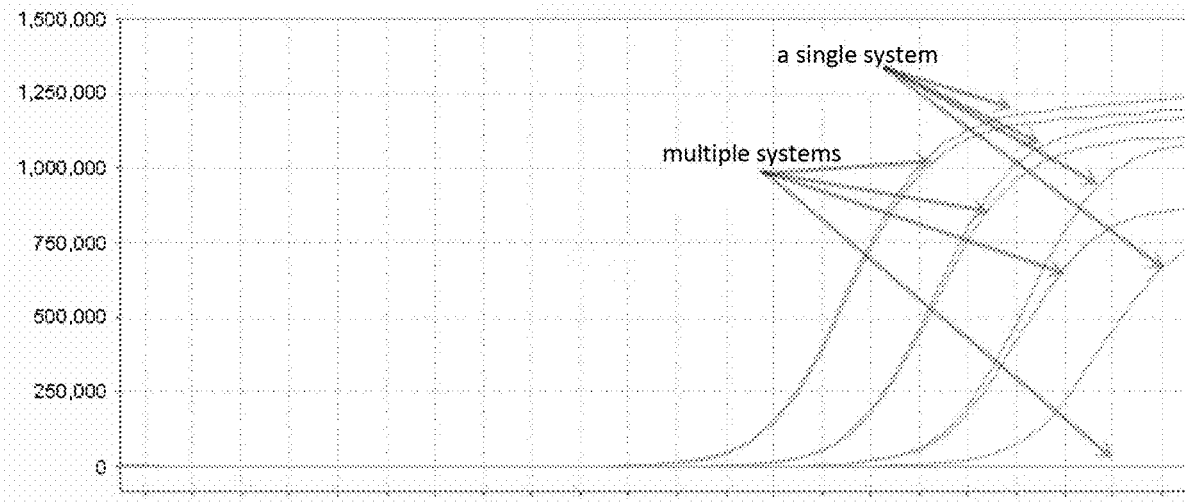
FIG. 14: Detection results for ORF1ab gene using control primer pair.

The detection results using ORF1ab-F2 and ORF1ab-R2 were shown in FIG. 13, and the detection results indicate that the primer pair had poor specificity. The detection results using ORF1ab-F3 and ORF1ab-R3 indicated that the primer pair had better specificity and sensitivity to the ORF1ab gene target nucleic acid in a single detection system. However, in the multiple detection system, the amplification of low concentration nucleic acid of ORF1ab gene was significantly inhibited. The results of single and multiple systems tests were shown in FIG. 14. This indicated that the control primer pairs ORF1ab-F3 and ORF1ab-R3 cannot be used in multiplex detection systems.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

What is claimed is:

1. A kit for multiplex detection of SARS-CoV-2 nucleic acid, which comprises:
   (1) a first primer pair for the detection of ORF1ab nucleic acid comprising an ORF1ab-F1 primer consisting of SEQ ID NO: 1 and an ORF1ab-R1 primer consisting of SEQ ID NO: 2;
   (2) a second primer pair for the detection of N nucleic acid comprising a N-F1 primer consisting of SEQ ID NO: 4 and a N-R1 primer consisting of SEQ ID NO: 5;
   (3) a first probe (ORF1ab-P) for the detection of ORF1ab nucleic acid consisting of SEQ ID NO: 3; and
   (4) a second probe (N-P) for the detection of N nucleic acid consisting of SEQ ID NO: 6; wherein the first and the second probe each contains a fluorescent reporter group that is different from each other at the 5' end and a fluorescence quenching group at the 3' end.

2. The kit of claim 1, wherein the fluorescent reporter group is selected from the group consisting of FAM, VIC, HEX, NED, ROX, TET, JOE, TAMRA, CY3, and CY5, and the fluorescence quenching group is selected from the group consisting of MGB, BHQ-1, BHQ-2, and BHQ-3.

3. The kit of claim 1, wherein the kit further comprises an internal standard primer pair
   comprising an internal standard-F1 primer consisting of SEQ ID NO: 7 and an internal standard-R1 primer consisting of SEQ ID NO: 8; and
   an internal standard-P probe consisting of SEQ ID NO: 9, wherein the first probe, the second probe, and the internal standard-P probe each contains a fluorescent reporter group that is different from each other at the 5' end and a fluorescence quenching group at the 3' end.

4. The kit of claim 1, wherein the kit comprises a first container, and the first container contains a primer and probe mix, and the primer and probe mix contains polynucleotides having sequences shown in SEQ ID NOs: 1 to 6.

5. The kit of claim 4, wherein the primer and probe mix further contains polynucleotides having sequences shown in SEQ ID NOs: 7 to 9.

6. The kit of claim 4, wherein the kit further comprises a second container, the second container contains a PCR enzyme system, and the PCR enzyme system includes a hot-start enzyme and a reverse transcriptase C-MMLV.

7. The kit of claim 6, wherein the second container further contains an RNA enzyme inhibitor.

8. The kit of claim 4, wherein the kit further comprises a third container, and the third container contains a positive control.

9. The kit of claim 4, wherein the kit further comprises a fourth container, and the fourth container contains a negative control.

10. The kit of claim 4, wherein the primer and probe mix further contains dNTPs.

11. A multiplex PCR method for the detection of SARS-CoV-2 nucleic acids comprising:
    1) extracting a nucleic acid template from a subject test sample;
    2) mixing the nucleic acid template with a PCR reaction system comprising the following components:
       a first primer pair for the detection of ORF1ab nucleic acid comprising an ORF1ab-F1 primer consisting of SEQ ID NO: 1 and an ORF1ab-R1 primer consisting of SEQ ID NO: 2;
       a second primer pair for the detection of N nucleic acid comprising a N-F1 primer consisting of SEQ ID NO: 4 and a N-R1 primer consisting of SEQ ID NO: 5;
       an internal standard-F1 primer consisting of SEQ ID NO: 7 and an internal standard-R1 primer consisting of SEQ ID NO: 8;
       a first probe (ORF1ab-P) for the detection of ORF1ab nucleic acid consisting of SEQ ID NO: 3;
       a second probe (N-P) for the detection of N nucleic acid consisting of SEQ ID NO: 6; and
       an internal standard-P probe consisting of SEQ ID NO: 9; wherein the first probe, the second probe, and the internal standard-P probe each contains a fluorescent reporter group that is different from each other at the 5' end and a fluorescence quenching group at the 3' end;
    3) performing a real-time fluorescent PCR; and
    4) detecting an amplified DNA using different fluorescent channel curves.

12. The method of claim 11, wherein the subject test sample is a pharyngeal swab sample, an alveolar lavage fluid sample, a blood sample, a sputum sample, or an environmental sample.

13. The method of claim 11, wherein the fluorescent reporter group is selected from the group consisting of FAM, VIC, HEX, NED, ROX, TET, JOE, TAMRA, CY3, and CY5, and the fluorescence quenching group is selected from the group consisting of MGB, BHQ-1, BHQ-2, and BHQ-3.

* * * * *